(12) United States Patent
Lovett

(10) Patent No.: US 6,434,417 B1
(45) Date of Patent: Aug. 13, 2002

(54) METHOD AND SYSTEM FOR DETECTING CARDIAC DEPOLARIZATION

(75) Inventor: Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/535,872

(22) Filed: Mar. 28, 2000

(51) Int. Cl.⁷ .............................................. A61B 5/0452
(52) U.S. Cl. ...................... 600/509; 600/515
(58) Field of Search ................ 600/509, 515, 600/521; 128/901; 607/1–2, 4–5, 7, 9, 25–26

(56) References Cited

U.S. PATENT DOCUMENTS

| | | | |
|---|---|---|---|
| 3,828,768 A | * 8/1974 | Douglas | 600/515 |
| 3,939,824 A | 2/1976 | Arneson et al. | 128/2.05 A |
| 3,998,214 A | * 12/1976 | Garrison | 600/515 |
| 4,000,461 A | 12/1976 | Barber et al. | 324/102 |
| 4,945,917 A | * 8/1990 | Akselrod et al. | 600/509 |
| 5,411,529 A | 5/1995 | Hudrlik | 607/6 |
| 5,417,221 A | 5/1995 | Sickler | 128/696 |
| 5,447,519 A | 9/1995 | Peterson | 607/5 |
| RE35,148 E | * 1/1996 | Lizzi | 348/163 |
| 5,682,902 A | 11/1997 | Herleikson | 128/708 |
| 5,738,104 A | * 4/1998 | Lo et al. | 128/706 |
| 5,738,105 A | 4/1998 | Kroll | 128/708 |
| 5,778,881 A | 7/1998 | Sun et al. | 128/696 |
| 5,957,857 A | * 9/1999 | Hartley | 600/521 |
| 5,984,954 A | 11/1999 | Cohen | 607/521 |
| 6,161,037 A | 12/2000 | Cohen | 600/513 |

OTHER PUBLICATIONS

Afonso et al., Multirate Processing of the ECG using Filter Banks, 1996, Computers in Cardiology, 245–248.*
Afonso et al., Filter Bank Based ECG Beat Detection, 1996, IEEE, 1037–1038.*
Afonso et al., Filter Bank Based ECG Beat Classification, 1997, IEEE, 97–100.*
Afonso et al., Filter Bank Based Processing of the Stress ECG, 1997, IEEE, 887–888.*
Valtino X. Afonso et al. ECG Beat Detection Using Filter Banks, Feb. 1999, IEEE Transactions on Biomedical Engineering vol. 46. No. 2 pp. 192–202.*

* cited by examiner

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

A system and method for detection of specific cardiac depolarization events, such as atrial and ventricular beats. Cardiac electrical activity is sensed to generate a sense signal that is decomposed into components by orthogonal filters. Statistical features are extracted from the components and analyzed to detect a specific event. In one embodiment, the sense signal is decomposed into frequency components by bandpass filtering. The design of the bandpass filters is such that the frequency components can be analyzed to determine whether they match the frequency components of a template signal corresponding to the specific cardiac depolarization event.

25 Claims, 2 Drawing Sheets

METHOD AND SYSTEM FOR DETECTING CARDIAC DEPOLARIZATION

FIELD OF THE INVENTION

This invention pertains to systems and methods for detecting bioelectrical activity. In particular, the invention relates to systems and methods for discriminating between cardiac depolarization and other sensed signals.

BACKGROUND

Cardiac rhythm management devices, such as pacemakers and implantable cardioverter/defibrillators, must accurately detect heart beats resulting from cardiac depolarization in order to perform their function. Such beat detection involves sensing a signal and then distinguishing between a signal due to cardiac depolarization and a noise signal due to either other cardiac electrical activity (e.g., abnormally conducted impulses, repolarization) or external noise. External noise sources that can generate sensed signals include electromagnetic fields in the environment and potentials produced by the patient's muscular activity. A common method for reducing the risk of mistaking one of these noise signals for a cardiac depolarization is to use a sensing threshold designed to be above the average amplitude of the noise signal but below a depolarization signal. In conventional pacemakers with sensing channels for sensing one or more heart chambers, the sensing channels must also distinguish between ventricular and atrial depolarizations. One way of facilitating this is to render a sensing channel refractory following certain events. (The term "refractory" means a no sensing condition when applied to a sensing channel, to be distinguished from the physiological refractory period of excitable tissue.) Sensing channels are rendered refractory both in order to prevent reentry into the system of an output pacing pulse (in which case the sensing amplifiers are blanked) and to prevent the misinterpretation of input data by the sensing of afterpotentials or by crosstalk between sensing channels.

Both of the above-mentioned methods for reducing the risk of oversensing, however, necessarily increase the risk of undersensing, i.e., that a depolarization event will fail to be detected. The present invention is directed toward an improved method for beat detection and discrimination that reduces the need for sensing thresholds and refractory periods.

SUMMARY OF THE INVENTION

The present invention is a system and method for detecting specific depolarization events such as occur in cardiac or other excitable tissue. It is particularly applicable to implantable cardiac devices such as pacemakers that function in response to detected heart beats, where the sensing channels of such devices are configured to sense either atrial or ventricular electrical activity in order to generate pacing pulses according to a programmed pacing mode. In accordance with the invention, cardiac electrical activity is sensed by a sensing channel to generate a sense signal. The sense signal is then processed in order to detect a specific cardiac depolarization event, such as a ventricular or atrial depolarization, by decomposing the signal into linearly independent components using orthogonal filters. A feature representing a statistical characteristic is then extracted from each signal component in synchronous fashion. The resulting feature set can then be compared with feature sets extracted from known signals (referred to as template signals) in order to identify the signal as a specific depolarization event.

In an exemplary embodiment, the sense signal is decomposed into multiple frequency components by a bandpass filter bank having passbands that correspond to the frequency components of a template signal that represents the specific cardiac depolarization event that is to be detected. In order to emphasize the high frequency components reflective of a change in signal energy, the frequency components of the sense signal are differentiated to extract a derivative signal therefrom. The sense signal frequency components are then amplitude demodulated to detect envelope signals representative of the signal energy changes in each of the passbands. The envelope signals are processed to determine if the signal energies of the passband frequency components of the sense signal increase in a phase-locked fashion. In a particular embodiment, the envelope signals are synchronously combined together by multiplying to generate a composite signal that is indicative of the detection of a depolarization event. In this manner, a cardiac depolarization event, such as an atrial or ventricular heart beat, can be reliably detected and discriminated from other signals.

DETAILED DESCRIPTION OF THE INVENTION

In a presently preferred embodiment, the present invention is a system and method for detecting specific depolarization events occurring in excitable tissue by analyzing the frequency-specific changes in signal energy of a sense signal. The invention may be employed for the detection of, for example, specific neural or cardiac depolarization events. In the latter case, a cardiac depolarization event corresponds to a heart beat. One of the objectives of beat detection is to discriminate between signal due to depolarization and that due to noise. Unlike most noise sources, depolarization exhibits a time-frequency signature that can be quantified with bandpass filters. Specifically, due to its impulse-like nature, depolarization consists of a rapid, broadband increase in signal energy. Cardiac depolarization thus results in phase-locked increases in signal energy over a broad range of frequencies. This characteristic property can be used both for the detection of depolarization signals generally (i.e., beat detection) and for discriminating between specific depolarization waveforms. The present invention takes advantage of this property of depolarization to discriminate between depolarization waveforms and other types of waveforms by detecting whether the signal energies in selected frequency bands of a sense signal increase in phase. The selected frequency bands correspond to the frequency content of the depolarization event that is to be detected, referred to as a template signal, and thus constitute a kind of frequency signature. Depolarization waveforms with different morphologies can also be discriminated by comparing the results of multiple detectors to distinguish between waveforms having different frequency signatures.

Figure 1:
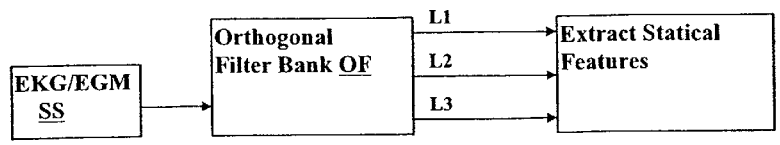
FIG. 1 is a block diagram showing the components of a signal processing system for detecting depolarization waveforms.

In a particular general formulation, the present invention involves the extraction of specific features from the input sense signal that can be used to identify the signal. An orthogonal filter bank decomposes the sense signal into separate linearly independent components, and a parameter describing the statistical behavior of each such component signal is synchronously extracted from each component to result in a feature set. The feature extraction may be performed for each component synchronous with a trigger signal such as a sensed cardiac signal; For example, the trigger signal may be derived from the sense signal itself or a companion signal (e.g., an atrial or ventricular rate channel). Statistics for each component are then extracted by performing a computation over a specified time period with respect to the trigger signal (e.g., +/−50 ms around the trigger). Examples of such statistics include a single sample point, mean, mode, variance, range interquartile range, and a mean square. In the case of a mean square statistic computed on signal components that are the outputs of bandpass filters (when the sense signal has zero mean), for example, the feature extraction operation is identical to computing a discrete power spectrum of the sense signal at the center frequencies of the filter passbands. The feature set in that case is thus literally a spectral signature of the sense signal. In order to detect or identify a specific sense signal, the extracted feature set is compared with a feature set derived from a template signal. If the extracted feature set sufficiently matches the template feature set, the sense signal can then be identified. FIG. 1 shows a block diagram of the steps involved. A sense signal SS is decomposed into linearly independent components L1 through L3 by an orthogonal filter bank OF. Statistical features are then synchronously extracted from each of the components and compared with features extracted from a template signal to determine if they match. The template signal and its features may be represented by choosing the filters of the orthogonal filter to correspond to characteristic linearly independent components of the template signal. In that case, the degree of match between the sense signal and the template signal can be determined by processing the extracted features to determine if all are present. One method of doing this is to cross-correlate the extracted features. For example, if the features represent average signal energy over time, multiplying the features together and integrating gives a composite signal representative of the degree to which components derived from each of the orthogonal filters are present.

In the particular embodiment of the invention to be described in more detail below, the orthogonal filters are bandpass filters with non-overlapping passbands, and the linearly independent components are the frequency components of the sensed signal. The bandpass filters that decompose the sensed signal into its different frequency components have passbands that correspond to the frequency components of the template depolarization signal. Envelope signals representing the changes in energy content of each of the frequency bands over time are then derived. The envelope signals thus constitute a statistical feature of each frequency component. The envelope signals are combined into a composite signal such that an increase in the amplitude of the composite signal indicates that the signal energies of the sense signal frequency components have undergone a phase-locked increase, which is a characteristic feature of depolarization. If the filter bank is constructed so as to emphasize characteristic features of the template signal (e.g., by the passbands of the filters representing characteristic frequency components of the template signal), the composite signal is indicative of how well the sense signal matches the template signal.

The template signal may be representative of the atrial or ventricular depolarization waveform that is sensed by a sensing channel with an atrial or ventricular electrode, respectively, during a normal heart beat. In that situation, the invention allows for enhanced beat detection that reduces the probability of missensing by a sensing channel. Such missensing can result from oversensing, when noise from external or myopotential sources is mistaken for a cardiac depolarization, or from crosstalk between sensing channels when cardiac activity is sensed that is intended to be sensed only by another sensing channel. This is accomplished without resorting to the usual way of reducing missensing by lengthening a refractory period of the sensing channel or raising the sensing threshold, both of which increase the risk of undersensing. The template signal may also represent the morphology of other kinds of abnormal specific depolarization waveforms that are of clinical significance. One application of this kind of signal discrimination is for detecting both arrhythmias and rhythms that may predispose to an arrhythmia. An implantable cardioverter/defibrillator, for example, may detect such rhythms in order to terminate or prevent an arrhythmia by delivering a defibrillation shock or anti-tachycardia pacing.

Figure 2A:
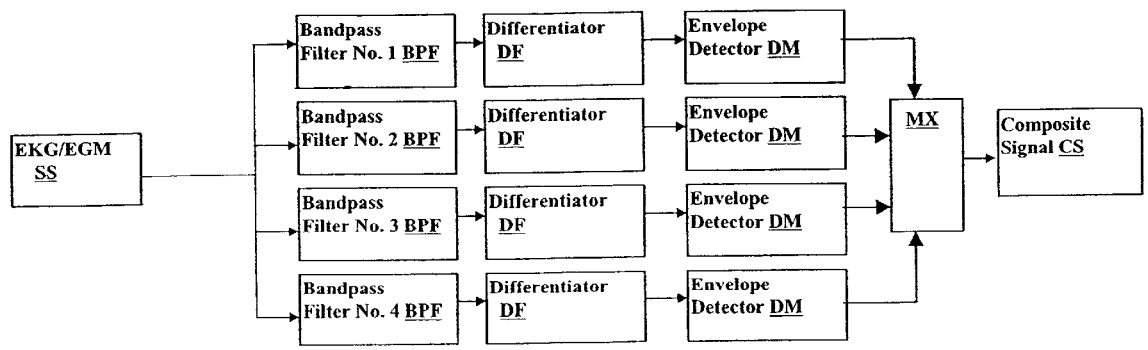
FIGS. 2A and 2B are block diagrams showing particular implementations.

FIG. 2A shows a block diagram of the components of a system in accordance with the invention that performs such processing. The sense signal SS to the system is the sense signal produced by a sensing channel that senses cardiac electrical activity, and may be either a surface electrocardiogram or an internally recorded electrogram. The signal SS is first decomposed into different frequency components by a bank of bandpass filters BPF that preferably exhibit linear phase frequency responses. The passbands of the filter bank are selected to correspond to the frequency components of a template signal that represents the event to be detected. Such an event may be a depolarization as distinguished from a noise signal (i.e., beat detection), or may be the occurrence of a depolarization with a specific waveform morphology. Event detection thus involves discriminating the sense signal from either noise or some other type of signal. The output signals of the filter bank represent those frequency components of the sense signal that are also present in some degree in the template signal. In the case of normal beat detection, the frequency content of a ventricular depolarization is broadly distributed from about 0 to 50 Hz. (A ventricular depolarization also has higher frequency content, but the signal-to-noise ratio is poor above 50 Hz and especially at multiples of 60 Hz due to line noise.) A template signal representing such a depolarization would therefore have a similar frequency content, and the passbands of the filter bank corresponding to the template signal would be contiguous divisions of the 0–50 Hz frequency range. The detection of the broadband depolarization signal may be optimized in certain embodiments by selecting passbands with the best signal-to-noise ratio (e.g., 10–50 Hz instead of 0–50 Hz to reduce 1/f noise or noise due to a patient's respiratory activity).

In the presently described embodiment, the extracted frequency component signals of the sense signal that are output from the bandpass filters BPF are next differentiated by differentiators DF in order to emphasize the higher frequencies representing a change in signal energy. Detection of a particular cardiac depolarization event depends on recognizing the phase-locked increases in signal energies over the range of frequencies passed by the bandpass filters. The derivative signals from the differentiators DF are next amplitude demodulated by demodulators DM to translate the frequencies of the derivative signals to a baseband range where the signals can be correlated. The amplitude demodulator DM may be an envelope detector comprising a full-wave rectifier and low pass filter that forms an envelope signal from the differentiated frequency component signals. The resulting envelope signals thus represent the change in signal energy of the sense signal over the range of frequencies represented by the passbands of the filter bank. In order to detect whether the sense signal matches the template signal, the envelope signals are multiplied together by mixers MX to give a composite signal CS that is sensitive to changes in the sense signal amplitude that increase the energy content in all of the envelope signals in phase. The composite signal CS is approximately zero during quiescent periods and increases with frequency-specific amplitude changes in the envelope signals as they occur. Thus the amplitude of the composite signal is indicative of the degree to which the sense signal matches the template signal as compared in the frequency domain if the passbands of the bandpass filters are chosen to correspond to characteristic frequency components of the template signal. In certain cases, the frequency components of multiple beat types are sufficiently similar that the composite signal method of detection just described may not be adequate. In such cases, extracting a more thorough statistical description of each filter output and comparing it with a template or templates may produce better results in discriminating between similar beats.

It should be appreciated that the amplitudes of the envelope signals, and of the composite signal, also depend upon the amplitude of the sense signal. In order for the amplitude of the composite signal to represent only the extent to which the frequency components of the sense and template signals match, an automatic gain control amplifier at the input of the system can be used to compensate for varying sense signal strength. Alternatively, a variable amplitude threshold for the composite signal that is used to detect a match between the sense signal and the template signal can be employed. The amplitude threshold is then made dependent upon the sense signal strength.

Figure 2B:
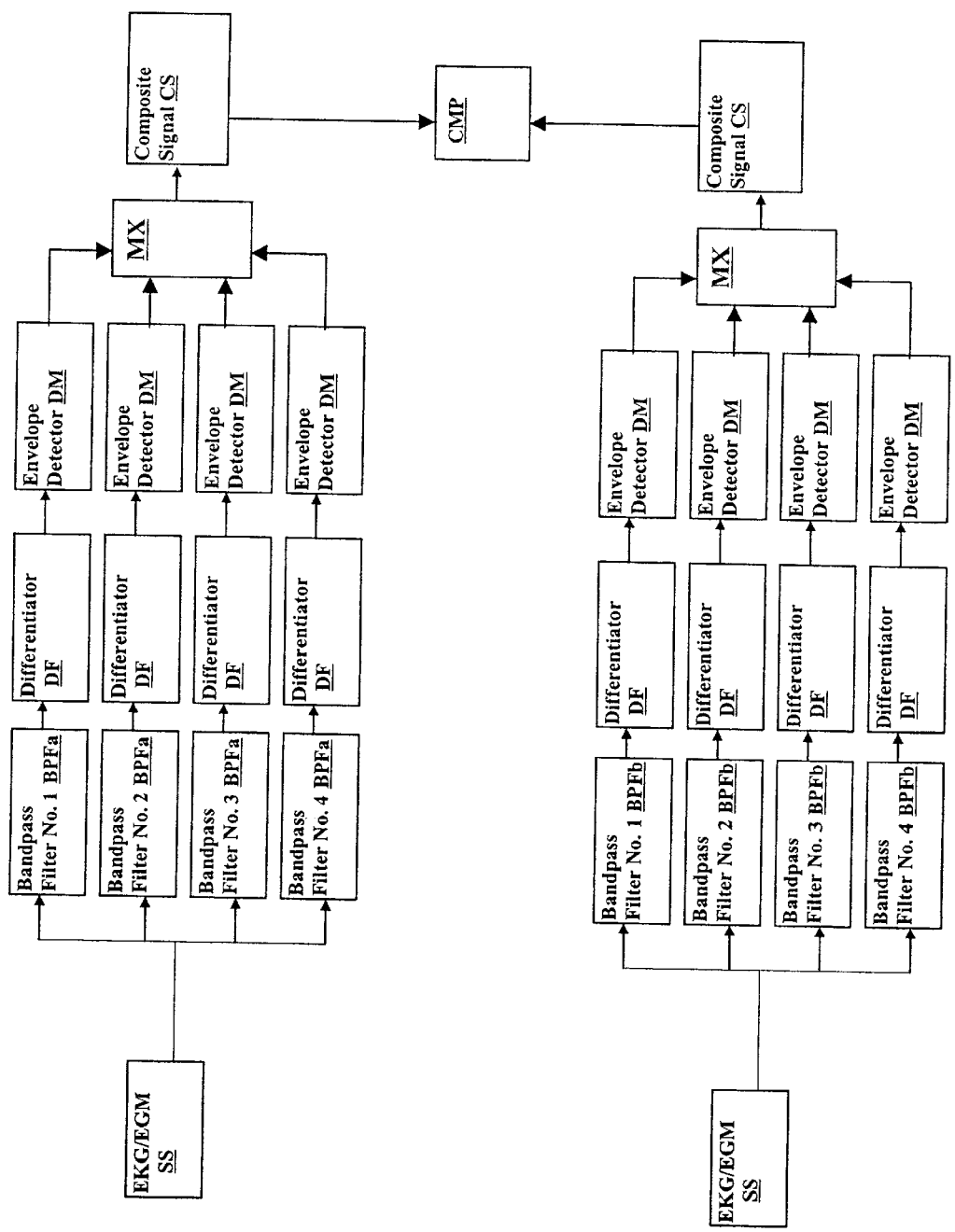

As aforesaid, it is the phase-locked increase in signal energy over specific frequency bands produced by depolarization that allows true depolarization to be discriminated from noise by the present method. A similar technique can be used for waveform morphology discrimination in order to detect a specific depolarization waveform. For example, since abnormally conducted heart beats often contain disproportionate amounts of low-frequency energy, two detectors can be used in tandem in order to detect such an event. A wide-band detector such as described above is used to detect normal beats, while another detector with low-frequency emphasis (as determined by the passbands of the detector's filter bank) detects both normal and ectopic beats. A detected heart beat could then be classified as ectopic when a beat is detected by the low-frequency detector but not by the wide-band detector. FIG. 2B shows a wide-band detector with a first bank of bandpass filters BPFa for decomposing the sense signal into multiple frequency components and a low-frequency detector with a second filter bank BPFb having passbands that pass a lower frequency range than the frequency range of the first filter bank. A comparator CMP compares the composite signals CS of each detector to detect ectopic beats. Similarly, other cardiac depolarization events with characteristic frequency signatures can be detected with multiple detectors and by proper design of the filter bank passbands in each of the detectors to constitute frequency signatures for the depolarization waveforms that are to be discriminated.

Figure 3:
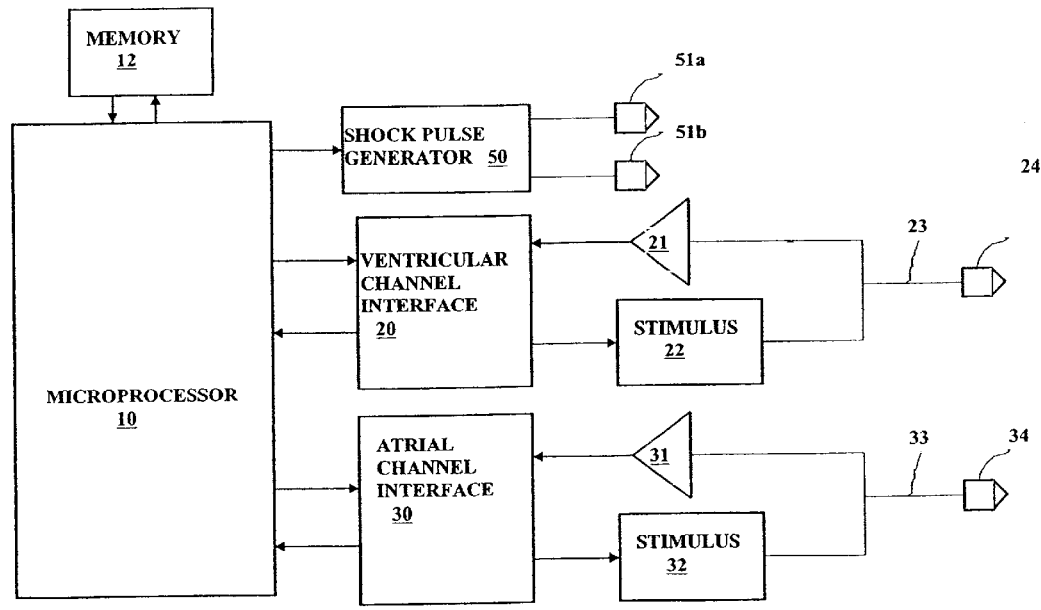
FIG. 3 is a diagram of a cardiac rhythm management device in which may be incorporated a system in accordance with the invention.

FIG. 3 is a system diagram of a microprocessor-based cardiac rhythm management device, which in this case is an implantable cardioverter/defibrillator (ICD) with the capability of also delivering pacing therapy. Such a device is capable of conventional bradycardia pacing as well as arrhythmia termination. A microprocessor 10 communicates with a memory 12 via a bidirectional data bus. The memory 12 typically comprises a ROM for program storage and a RAM for data storage. The device has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. The sensing channels sense cardiac electrical activity from an electrode placed in proximity to a particular region of the heart and produce a sense signal in accordance therewith. A shock pulse generator 50 is also interfaced to the microprocessor for delivering cardioversion or defibrillation pulses to the heart via a pair of terminals 51a and 51b that are connected by leads to shock electrodes placed in proximity to regions of the heart. The shock electrodes could also be used for sensing as well as pacing or defibrillation, in which case another sensing amplifier would be included (not shown).

The present invention can be used to advantage by the device in either its pacemaker or arrhythmia treatment/prevention capacity, and can be used in conjunction with other methods of beat/arrhythmia detection (e.g., where one technique is used as a backup). As described above, the passbands of the bandpass filter bank can be configured to correspond to a template signal, allowing the comparison of a sense signal with the template signal in the frequency domain. In performing its pacing function, the device generates pacing pulses in response to lapsed time intervals and sensed cardiac electrical activity in order to pace the heart according to a programmed pacing mode. As it is critical to the proper operation of a pacemaker that sensed signals be interpreted correctly, the present invention provides a way to prevent missensing without resorting to increased refractory periods by comparing the sense signal with a template signal that is representative of either ventricular or atrial depolarization for the ventricular and atrial sensing channels, respectively. The device also monitors the heart through the sensing channels in order to detect arrhythmias, or rhythms predictive of an incipient arrhythmia, which can be treated with either a defibrillation pulse or anti-tachycardia pacing. Analysis of the morphology of the sensed waveform can be used to aid in the recognition of such rhythms, which can be performed by comparing the sense signal to a template signal representative of a particular arrhythmia.

Each of the channel interfaces include signal conditioning circuitry and an analog-to-digital converter for producing digitized samples of the sensed waveform that can be analyzed to detect a depolarization corresponding to the template signal. In an alternate embodiment, the sense signal is decomposed into frequency components in the analog domain using analog filters and mixers, and the resulting composite signal may then be digitized for inputting into digital circuitry. In the present embodiment, however, the digitized sense signal is input to signal processing circuitry that performs the signal discrimination method as described above. Such signal processing circuitry can be a dedicated digital signal processor or the same processor used to control the device. Thus, a system in accordance with the invention may be incorporated into the device of FIG. 2 as code executed by the microprocessor 10. The following are representative code samples of an exemplary implementation of the signal processing components shown in FIG. 1.

In this particular implementation, the sense signal is a digitized data stream contained in an array designated data[i]. Three bandpass filters are used with passbands of 25–50 Hz, 12.5–25 Hz, and 6.25–12.5 Hz. The bandpass filters are implemented by dividing the sense signal into four simultaneous data streams, passing the streams through low-pass filters having roll-off frequencies that correspond to the boundaries of the desired passbands, and forming the bandpass filter output signals from subtractive combinations of the low-pass filter outputs. The low-pass filters are implemented as linear phase moving average filters. Next, the bandpass filter outputs, designated band1[i], band2[i], and band3[i], are differentiated with a first difference filter that also rectifies the signals. Another moving average filter completes the demodulation process to give three envelope signals, designated demo1[i], demo2[i], and demo3[i]. Multiplication of the envelope signals then results in the composite signal.

a. First, four simultaneous data streams are created and low-pass filtered:

```
for (i=0; i<16; i++) {
    ma32[i]=0;
    ma16[i]=0;
    ma08[i]=0;
    ma04[i]=0;
}
for (i=16; i<SAMPLESINMINUTE-16; i++) {
    ma32[i]=0;
    ma16[i]=0;
    ma08[i]=0;
    ma04[i]=0;
    for (j=-16; j<16; j++) // 32-point moving average, 40%
        power at 6.25 Hz
        ma32[i]+=data[i+j];
    for (j=-8; j<8; j++) // 16-point moving average, 40%
        power at 12.5 Hz
        ma16[i]+=data[i+j];
    for (=-4; j<4; j++) // 8-point moving average, 40% power
        at 25.0 Hz
        ma08[i]+=data[i+j];
    for (j=-2; j<2; j++) // 4-point moving average, 40% power
        at 50.0 Hz
        ma04[i]+=data[i+j];
    ma32[i]/=32;
    ma16[i]/=16;
    ma08[i]/=8;
    ma04[i]/=4;
}
for (i=SAMPLESINMINUTE-16; i<SAMPLESINMINUTE; i++) {
    ma32[i]=0;
    ma16[i]=0;
    ma08[i]=0;
    ma04[i]=0;
}
``` b. Next, the moving average data streams are used to construct bandpass signals:

```
for (i=0; i<SAMPLESINMINUTE; i++) {
    band1[i]=ma04[i]-ma08[i]; // bandpass from 25.0–50.0 Hz
    band2[i]=ma08[i]-ma16[i]; // bandpass from 12.5–25.0 Hz
    band3[i]=ma16[i]-ma32[i]; // bandpass from 6.25–12.5 Hz
}
``` c. Next, first differences of bandpass signals are constructed with rectification:

```
diff1[0]     = 0;
diff2[0]     = 0;
diff3[0]     = 0;
diff1[SAMPLESINMINUTE-1] = 0;
diff2[SAMPLESINMINUTE-1] = 0;
diff3[SAMPLESINMINUTE-1] = 0;
for (i = 1; i < SAMPLESINMINUTE - 1; i++) {
    diff1[i] = abs(band1[i] - band1[i-1]);
    diff2[i] = abs(band2[i] - band2[i-1]);
    diff3[i] = abs(band3[i] - band3[i-1]);
}
``` d. Another moving average filter completes the demodulation process:

```
for (i=0; i<8; i++) {
    demo1[i]=0;
    demo2[i]=0;
    demo3[i]=0;
}
for (i=8; i<SAMPLESINMINUTE-8; i++) {
    demo1[i]=0;
    demo2[i]=0;
    demo3[i]=0;
    for (j=-8; j<8; j++) {
        demo1[i]+=diff1[i+j];
        demo2[i]+=diff2[i+j];
        demo3[i]+=diff3[i+j];
    }
    demo1[i]/=16;
    demo2[i]/=16;
    demo3[i]/=16;
}
for (i=SAMPLESINMINUTE-8; i<SAMPLESINMINUTE; i++) {
    demo1[i]=0;
    demo2[i]=0;
    demo3[i]=0;
}
```

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for detecting a specific cardiac signal corresponding to a template signal, comprising:

a sensing channel for sensing cardiac electrical activity and outputting a sense signal in accordance therewith;

a first bank of bandpass filters for decomposing the sense signal into multiple frequency components, wherein the bandpass filters are selected with passbands corresponding to frequency components of the template signal;

a differentiator for extracting a derivative signal from each of the multiple frequency components of the sense signal;

an amplitude demodulator for detecting an envelope signal from each of the derivative signals; and, a multiplier for multiplying the envelope signals and outputting a composite signal in accordance therewith, the composite signal representing a correspondence between the sensed signal and the template signal.

2. The system of claim 1 wherein the sense signal is digitized, and the filter bank and amplitude demodulator are implemented digitally by a processor.

3. The system of claim 1 wherein the amplitude demodulator comprises a full-wave rectifier and low-pass filter.

4. The system of claim 1 wherein the sensing channel is configured to detect ventricular depolarizations.

5. The system of claim 1 wherein the sensing channel is configured to detect atrial depolarizations.

6. The system of claim 1 wherein the passbands of the bandpass filter bank are contiguous divisions of a frequency range between approximately 10 and 50 Hz to represent the frequency components of a cardiac depolarization.

7. The system of claim 1 wherein the passbands of the bandpass filter bank are contiguous divisions of a frequency range between approximately 0 and 50 Hz to represent the frequency components of a cardiac depolarization.

8. The system of claim 6 further comprising a second filter bank with passbands dividing a lower frequency range than the frequency range of the first filter bank, wherein the outputs of the second filter bank are multiplied together to form a second composite signal.

9. The system of claim 8 further comprising a comparator for comparing the first and second composite signals to detect ectopic beats.

10. A method for detecting a specific biological depolarization event, comprising:

sensing bioelectrical activity to generate a sense signal in accordance therewith;

filtering the sense signal with a first bank of orthogonal filters to thereby decompose the sense signal into linearly independent components;

synchronously extracting a statistical feature from each component of the sense signal; and, comparing the extracted features with features representing linearly independent components of a template signal corresponding to the specific depolarization event.

11. The method of claim 10 wherein the bank of orthogonal filters comprises a bank of bandpass filters for decomposing the sense signal into multiple frequency components, and wherein the bandpass filters are selected with passbands corresponding to frequency components of the template signal, the method further comprising:

extracting derivative signals from the multiple frequency components of the sense signal;

amplitude demodulating the derivative signals to detect an envelope signal from each of the derivative signals;

multiplying the envelope signals to thereby generate a composite signal representing detection of the specific depolarization event.

12. The method of claim 10 wherein the statistical features are extracted from the sense signal components in synchronization with a trigger signal.

13. The method of claim 12 wherein the trigger signal is a sensed cardiac signal.

14. A method for detecting a specific biological depolarization event, comprising:

sensing bioelectrical activity to generate a sense signal in accordance therewith;

filtering the sense signal with a first bank of bandpass filters to thereby decompose the sense signal into multiple frequency components, wherein the bandpass filters are selected with passbands corresponding to frequency components of a template signal representing the specific depolarization event;

extracting derivative signals from the multiple frequency components of the sense signal;

amplitude demodulating the derivative signals to detect an envelope signal from each of the derivative signals;

multiplying the envelope signals to thereby generate a composite signal representing detection of the specific depolarization event.

15. A processor-executable storage medium containing code for processing a sense signal in accordance with the method as set forth in claim 1.

16. The method of claim 1 wherein the biological depolarization. event is a cardiac depolarization event.

17. The method of claim 16 wherein the amplitude demodulation is performed by full-wave rectification and low-pass filtering.

18. The method of claim 16 wherein the specific depolarization event detected is a ventricular depolarization.

19. The method of claim 16 wherein the specific depolarization event detected is a atrial depolarization.

20. The method of claim 16 wherein the passbands of the bandpass filter bank are contiguous divisions of a frequency range between approximately 0 and 50 Hz to represent the frequency components of a specific cardiac depolarization event.

21. The method of claim 16 wherein the passbands of the bandpass filter bank are contiguous divisions of a frequency range between approximately 10 and 50 Hz to represent the frequency components of a specific cardiac depolarization event.

22. The method of claim 21 comprising:

filtering the sense signal with a second filter bank having passbands that pass a lower frequency range than the frequency range of the first filter bank; and, multiplying the outputs of the second filter bank together to form a second composite signal.

23. The method of claim 22 further comprising comparing the first and second composite signals to detect ectopic beats.

24. The method of claim 16 wherein the filtering, differentiation, and amplitude demodulation are performed digitally by a processor.

25. The method of claim 24 wherein the bandpass filtering is performed by combining the outputs of a plurality of moving average filters.

* * * * *